US009952189B1

(12) United States Patent
Chen et al.

(10) Patent No.: US 9,952,189 B1
(45) Date of Patent: Apr. 24, 2018

(54) IDENTIFYING INACCURACY IN AIR QUALITY DETECTION

(71) Applicant: ESMART TECH, INC., San Diego, CA (US)

(72) Inventors: Li Chen, Beijing (CN); Kenny Fok, San Diego, CA (US); David Diplock, Alpine, CA (US); Niral Bhalodia, San Diego, CA (US); Ying Xiong, San Diego, CA (US)

(73) Assignee: ESMART TECH, INC, San Diego, CA (US)

( * ) Notice: Subject to any disclaimer, the term of this patent is extended or adjusted under 35 U.S.C. 154(b) by 0 days.

(21) Appl. No.: 15/385,714

(22) Filed: Dec. 20, 2016

(51) Int. Cl.
*G01N 33/00* (2006.01)

(52) U.S. Cl.
CPC ....... *G01N 33/0073* (2013.01); *G01N 33/007* (2013.01)

(58) Field of Classification Search
CPC .................................................. G01N 33/0073
See application file for complete search history.

(56) References Cited

U.S. PATENT DOCUMENTS

| 4,868,546 | A | 9/1989 | Dumbeck |
| 5,520,328 | A | 5/1996 | Bujak, Jr. |
| 6,425,297 | B1 | 7/2002 | Sharp |
| 7,111,496 | B1 * | 9/2006 | Lilienfeld ............... G01N 21/51 356/338 |
| 7,302,313 | B2 | 11/2007 | Sharp et al. |
| 7,389,158 | B2 | 6/2008 | Desrochers et al. |
| 8,219,249 | B2 | 10/2012 | Harrod et al. |
| 8,963,726 | B2 * | 2/2015 | Kates ................. G01N 33/0065 340/577 |
| 2009/0190625 | A1 * | 7/2009 | Chung .................... G06F 1/206 374/11 |
| 2011/0316706 | A1 * | 12/2011 | Cash .................. B01D 46/0086 340/584 |
| 2013/0038470 | A1 | 2/2013 | Niemeyer et al. |
| 2014/0025208 | A1 * | 1/2014 | Allen-Ware ........ G06F 11/2023 700/276 |
| 2015/0032264 | A1 | 1/2015 | Emmons et al. |

(Continued)

FOREIGN PATENT DOCUMENTS

CN         203745015         7/2014

*Primary Examiner* — Manuel L Barbee
*Assistant Examiner* — Raymond Nimox
(74) *Attorney, Agent, or Firm* — TDFoster; Thomas D. Foster; Bruce Hare

(57) ABSTRACT

An automated method of detecting measurement inaccuracy in an air quality detection system includes: receiving an air quality measurement from at least two sensors; determining a difference among the received air quality measurements; and comparing the difference to a threshold value. A system that detects measurement inaccuracy in an air quality detection includes: multiple smart residue avoidance and inaccuracy detection (SRAID) devices; and a server. An SRAID device includes: a plurality of air quality detection sensors; a controller able to: receive measurements from the plurality of air quality detection sensors; calculate a difference among the received measurements; and generate a notification if the difference exceeds a threshold value; and a communication module able to communicate with at least one of a server and an air flow controller device.

14 Claims, 5 Drawing Sheets

(56) References Cited

U.S. PATENT DOCUMENTS

| | | | |
|---|---|---|---|
| 2015/0032266 A1* | 1/2015 | Weast | B60H 1/008 700/276 |
| 2015/0067153 A1* | 3/2015 | Bhattacharyya | H04L 43/04 709/224 |
| 2015/0077737 A1* | 3/2015 | Belinsky | G01N 21/53 356/51 |
| 2015/0254958 A1* | 9/2015 | Sherman | G08B 21/18 340/607 |
| 2015/0370294 A1* | 12/2015 | Busch | G06F 1/206 713/322 |
| 2016/0116181 A1* | 4/2016 | Aultman | F24F 11/0017 700/276 |
| 2016/0146769 A1* | 5/2016 | Zhang | G01N 33/0073 73/31.02 |
| 2016/0277714 A1* | 9/2016 | Teachout | H04N 7/181 |
| 2016/0328945 A1* | 11/2016 | Greisser | F24F 11/006 |
| 2016/0378605 A1* | 12/2016 | Teshome | G06F 11/3062 714/36 |

* cited by examiner

IDENTIFYING INACCURACY IN AIR QUALITY DETECTION

CROSS-REFERENCE TO RELATED APPLICATIONS

This application claims priority to U.S. Provisional Patent Application Ser. No. 62/332,995, filed on May 6, 2016

BACKGROUND

Existing air quality detection equipment generally drives air flow through an air quality sensor using a mechanism such as a fan. Over time, residue is trapped within the air path and affect the accuracy of the air quality measurement.

Because the sensing environments are varied and dynamic, the accuracy degradation may not be able to be predicted based on elapsed time or other such measures. For instance, in a very polluted area, sensor accuracy may degrade below an acceptable level within one month while a less polluted area, the sensor may maintain acceptable accuracy for a year or more.

Therefore there exists a need for a way to determine accuracy degradation of air quality sensors.

SUMMARY

Some embodiments provide ways to detect and/or correct for air quality detection inaccuracies. Such inaccuracies may be due to residue buildup along an air flow pathways that affects the ability of at least some air quality detection sensors to lose accuracy.

A smart residue avoidance and inaccuracy detection (SRAID) device of some embodiments may include a set of air quality measurement sensors. Measurements received from the sensors may be compared to other sensors in the set and/or to sensors associated with other SRAID devices.

Some embodiments may calculate a difference among the received measurements. Such a difference may be compared to a threshold value. If the difference exceeds the threshold value, a notification may be generated indicating that there is a mismatch in received measurements. Such a notification may be sent to a server and/or relayed to an air flow control device such as a fan or turbine.

The notification may flag the mismatch (such that the flag may be indicated to a technician or other appropriate user) and/or provide (or direct) corrective action. For instance, some embodiments may increase fan speed or heat difference to attempt to dislodge residue associated with a measurement mismatch.

Some embodiments may operate using a local closed loop. In such cases, a single SRAID device (and/or multiple local devices) may identify a mismatch and either flag the mismatch or attempt corrective action in the local environment (e.g., by directing a fan to increase flow speed along the measurement pathway).

Some embodiments may operate using a wide area closed loop. In such cases, measurements from one SRAID device may be compared to measurements from a number of associated SRAID devices. Such devices may be associated based on various relevant factors (e.g., geographic location, system association, device type, etc.). If a mismatch is identified, notification may be sent to the affected device(s) and/or users. Alternatively, a corrective action may be initiated by a server or other appropriate device associated with the wide area closed loop.

The preceding Summary is intended to serve as a brief introduction to various features of some exemplary embodiments. Other embodiments may be implemented in other specific forms without departing from the scope of the disclosure.

BRIEF DESCRIPTION OF THE SEVERAL VIEWS OF THE DRAWINGS

The exemplary features of the disclosure are set forth in the appended claims. However, for purpose of explanation, several embodiments are illustrated in the following drawings.

DETAILED DESCRIPTION

The following detailed description describes currently contemplated modes of carrying out exemplary embodiments. The description is not to be taken in a limiting sense, but is made merely for the purpose of illustrating the general principles of some embodiments, as the scope of the disclosure is best defined by the appended claims.

Various features are described below that can each be used independently of one another or in combination with other features. Broadly, some embodiments generally provide ways to monitor, evaluate, and direct air quality detection equipment.

A first exemplary embodiment provides an automated method of detecting measurement inaccuracy in an air quality detection system, the method comprising: receiving an air quality measurement from at least two sensors; determining a difference among the received air quality measurements; and comparing the difference to a threshold value.

A second exemplary embodiment provides a system that detects measurement inaccuracy in an air quality detection, the system comprising: a plurality of smart residue avoidance and inaccuracy detection (SRAID) devices; and a server.

A third exemplary embodiment provides an SRAID device comprising: a plurality of air quality detection sensors; a controller able to: receive measurements from the plurality of air quality detection sensors; calculate a difference among the received measurements; and generate a notification if the difference exceeds a threshold value; and a communication module able to communicate with at least one of a server and an air flow controller device.

Several more detailed embodiments are described in the sections below. Section I provides a description of various hardware architectures used by some embodiments. Section II then describes various methods of operation used by some embodiments. Lastly, Section III describes a computer system which implements some of the embodiments.

I. Hardware Architecture

Figure 1A:
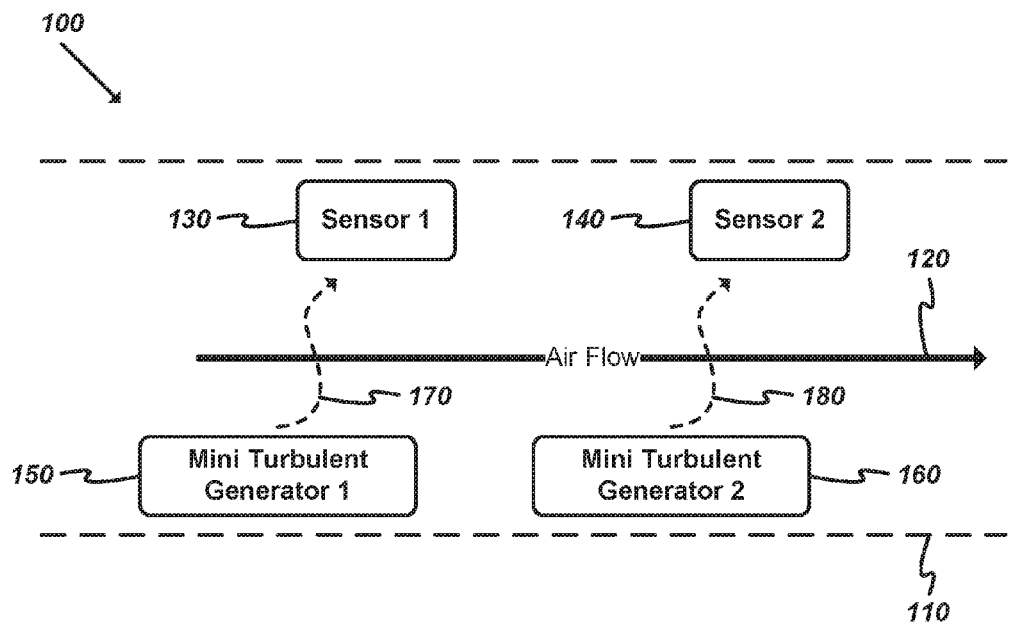
FIG. 1A illustrates a schematic block diagram of a localized detection system according to an exemplary embodiment.
Figure 1B:
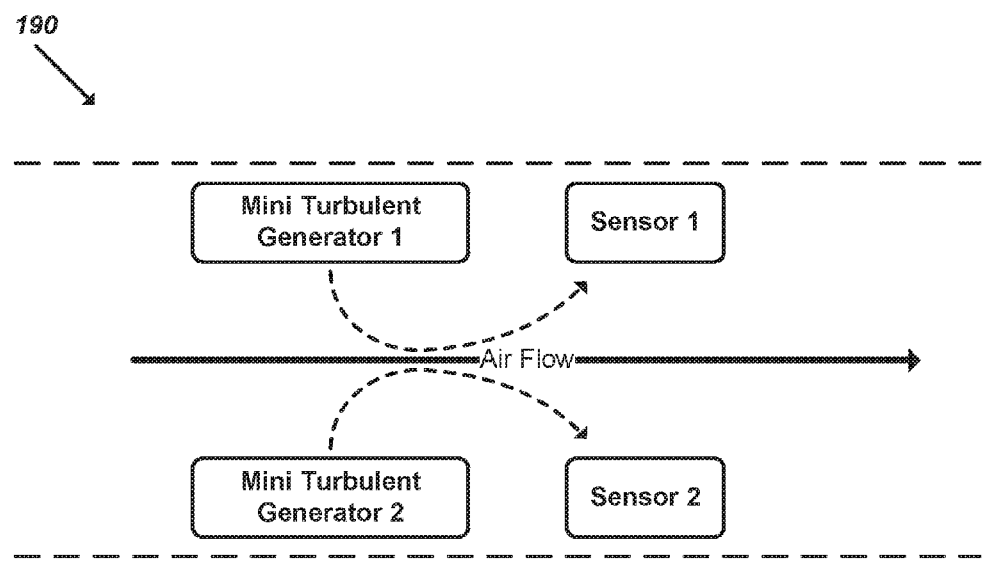
FIG. 1B illustrates a schematic block diagram of an alternative localized detection system according to an exemplary embodiment.

FIG. 1A illustrates a schematic block diagram of a localized detection system 100 according to an exemplary embodiment. FIG. 1B illustrates a schematic block diagram of an alternative localized detection system 190 according to an exemplary embodiment.

As shown, system 100 and system 190 may include a physical pathway 110 (e.g., a pipe, duct, etc.), air flow 120, a first sensor 130, a second sensor 140, a first turbulent generator 150, a second turbulent generator 160, a first mini turbulent 170, and a second mini turbulent 180.

As shown, pairs of air quality sensors 130-140 may be arranged in various configurations relatively to an air flow pathway 110 (or other fluid pathway) such that measurements may be taken at different locations along the pathway. In system 100, the sensors 130-140 and associated generators 150-160 are arranged in series along the pathway 120. In system 190, the sensors 130-140 and associated generators 150-160 are arranged in parallel along the pathway 120.

Each sensor 130 or 140 may be able to perform various air quality measurements and generate an analog and/or digital output representing the measurements. Each sensor 130 or 140 in the pair of sensors may perform the same type of measurement in order to be able to compare measured values between the sensors in the pair. Some embodiments may calculate a weighted average across multiple sensors for detection. Some embodiments may include a single sensor and utilize network data for detection.

The air flow 120 may be provided by a fan or other appropriate air flow controller device. The flow may include creating mini air turbulences 170 and 180 throughout the pathway 120 and directed at the locations of sensors 130 and 140. Such mini air turbulences may be generated using changes in mechanical design of a smooth flow air pathway (e.g., a step up or step down feature), creating an air temperature difference (e.g., by heating a portion of the pathway), and/or other appropriate ways (e.g., using generators 150-160).

One of ordinary skill in the art will recognize that the systems 100 and/or 190 may be implemented in various different ways without departing from the scope of the disclosure. For instance, some embodiments may include various additional elements, omit various elements, and/or arrange the elements in various different ways. In addition, the relative positions of the various elements may vary depending on various relevant factors (e.g., air distribution type, application type, sensor type, geographic location, environmental conditions, etc.).

Figure 2:
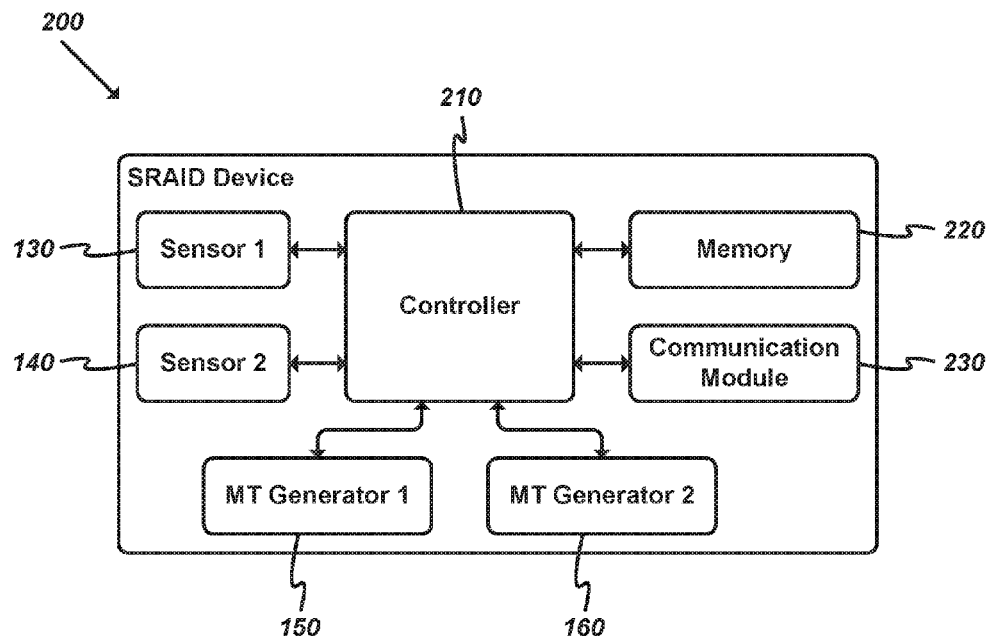
FIG. 2 illustrates a schematic block diagram of a detection device according to an exemplary embodiment.

FIG. 2 illustrates a schematic block diagram of an SRAID device 200 according to an exemplary embodiment. In this example, the device includes two sensors 130-140 and two mini turbulent generators 150-160 such as those described above, a controller 210, memory 220, and a communication module 230.

The device 200 may be distributed across multiple elements in some embodiments (e.g., the sensors 130-140 and/or generators 150-160 may be wirelessly connected to the controller 210 via the communication module 230). In addition, some embodiments may include additional elements (e.g., additional pairs of sensors associated with various other pathways or locations along the pathway) or omit various elements.

Other components may include a fan or other component able to direct or otherwise affect airflow. Such a fan may be able to be controlled by the controller (e.g., a fan or other air flow element may be activated, the speed of a fan may be changed, etc.).

The controller 210 may include various electronic devices and/or circuitry that are able to receive messages, data, and/or instructions from other system elements. The controller may be able to send messages, data, commands, and/or instructions to other system elements. The controller may be able to execute various sets of instructions, including programs or applications.

The memory 220 may include data and/or instructions used by the controller 210 to interact with the sensors 130-140 and/or generators 150-160, control the fan or other resource, direct the communication module 230, and/or otherwise used by the controller 210 to implement the various features.

The communication module 230 may allow the device to communicate with various external components (e.g., sensors, fans, etc.) and/or various network-accessible components.

One of ordinary skill in the art will recognize that the device 200 may be implemented in various specific ways without departing from the scope of the disclosure. For instance, the device may include additional components, omit various components, and/or arrange the components in various different ways. As another example, some components (e.g., controller 210) may be shared across devices 200. In some embodiments, the device 200 may include various user interface elements (e.g., touchscreens, knobs, buttons, keypads, etc.) that may allow a user to enter various operating parameters (and/or to view various displayed parameters).

Figure 3:
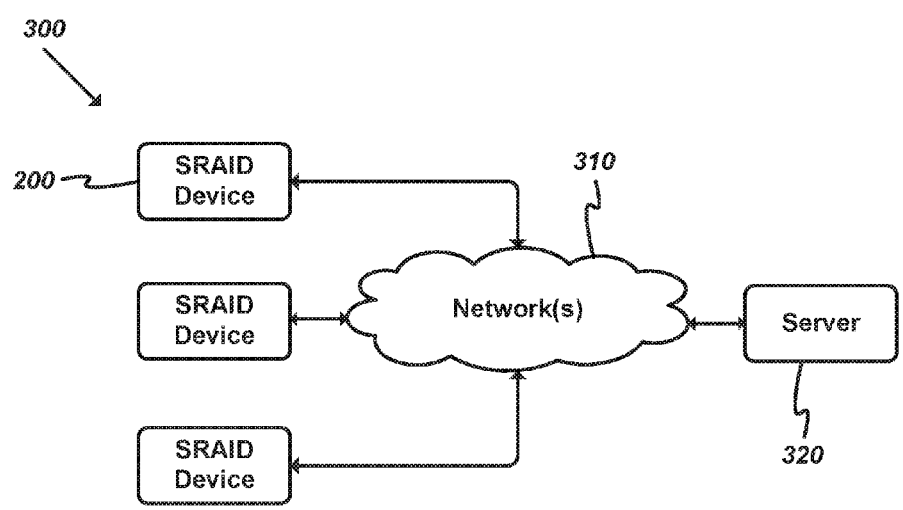
FIG. 3 illustrates a schematic block diagram of a distributed system according to an exemplary embodiment.

FIG. 3 illustrates a schematic block diagram of a distributed system 300 according to an exemplary embodiment. As shown, the system may include multiple devices 200, a set of networks 310, and a server 320.

In this example, the server 320 is able to interact with the various SRAID devices 200 across one or more networks 310. The networks may include wired networks (e.g., Ethernet), wireless networks (e.g., Wi-Fi, Cellular, radio, etc.), distributed networks (e.g., the Internet), and/or other appropriate communication pathways.

The server 320 may be a computing device that is able to receive data from the SRAID devices 200 and/or send data, commands, and/or instructions to the devices. The server 320 may be able to access various local and/or distributed storages and/or other accessible resources such as local resources or network accessible resources.

One of ordinary skill in the art will recognize that the system 300 may be implemented in various different ways without departing from the scope of the disclosure. For instance, some embodiments may include various additional elements, omit various elements, and/or arrange the elements in various different ways. In addition, various external servers, storages, etc. may be accessible to system 300. For instance, the server 320 may be able to direct and/or otherwise communicate with various external elements associate with the air quality detection systems (e.g., fans, heaters, etc.).

II. Methods of Operation

Figure 4:
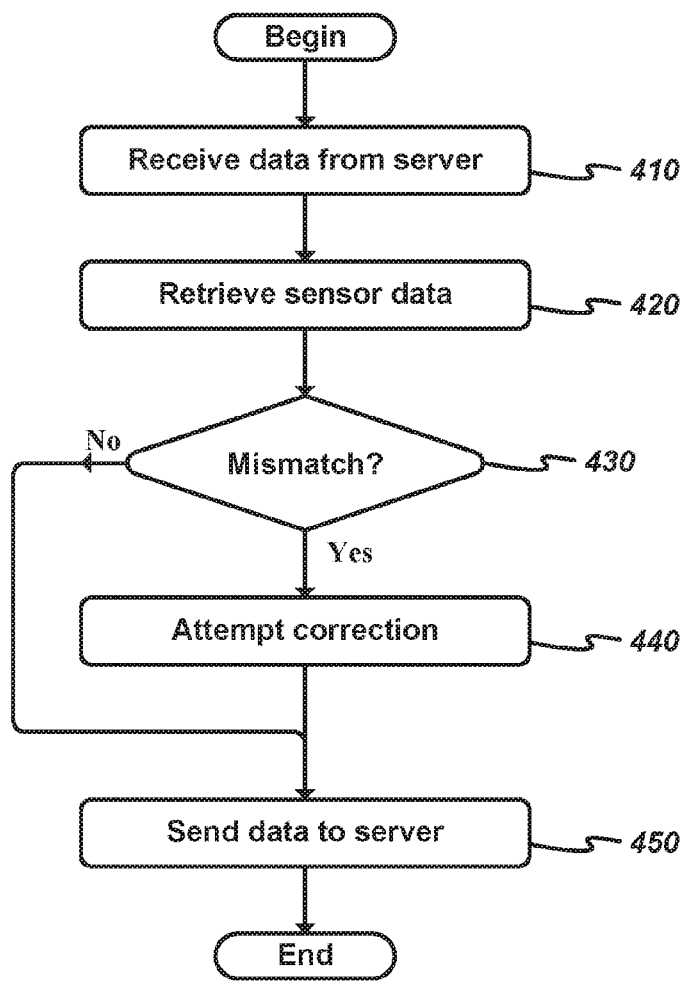
FIG. 4 illustrates a flow chart of an exemplary client-side process that monitors air quality detection equipment.

FIG. 4 illustrates a flow chart of an exemplary client-side process 400 that monitors air quality detection equipment. Such a process may be executed by a device such as SRAID device 200 and/or other appropriate elements. The process may begin, for instance, when an SRAID device of some embodiments is powered on.

As shown, process 400 may receive (at 410) data from a server, if available. A server, such as server 320) may send data, such as operating parameters, event thresholds, messages or commands, etc. that may be utilized by the SRAID device during operation. If no server or connection is available, the process may use a set of default parameters, user specified parameters, a most recent update, and/or other appropriate settings.

Next, the process may retrieve (at 420) sensor data. Such data may be retrieved from a pair of sensors placed in close proximity as described above. The data may include analog and/or digital signals.

The process may then determine (at 430) whether there is a mismatch in the retrieved data by comparing the retrieved data from each sensor (e.g., by calculating a difference between two measurements taken at or near the same time). Some embodiments may identify mismatches based at least partly on data received from the server. The mismatch determination may include various other operations and the resulting value(s) may be compared to one or more threshold values to determine whether an observed mismatch is within specified limits. Such threshold values, along with other operating parameters, may be configured in various appropriate ways (e.g., by receiving such values from a server, via default settings, local settings at a device, etc.).

If the process determines there is a mismatch that exceeds a particular threshold (or some other appropriate criteria is met), the process may attempt (at 440) to correct the mismatch. Such an attempt may include, for instance, increasing fan speed or changing temperature in an attempt to dislodge residue from a pathway. In some embodiments, the attempted correction may utilize various appropriate pathways or components (e.g., server and network connection) in order to control the operation of a fan or heating element external to the SRAID device, for instance. Such corrections may involve various appropriate messages, commands, etc. that may be relayed among the various devices.

Finally, the process may send (at 450) data to the server and then may end. Alternatively, the data may be stored locally for future transmission or other use. Such data may include, for instance, measurement data, correction data (including actions and results), device data (e.g., type of sensor, sensor ID, location, application setting, etc.), and/or other appropriate data.

In some embodiments, the SRAID devices and the server may form a two-way communication channel such that the server may receive data and send commands or other instructions to multiple devices as the system is operated.

Figure 5:
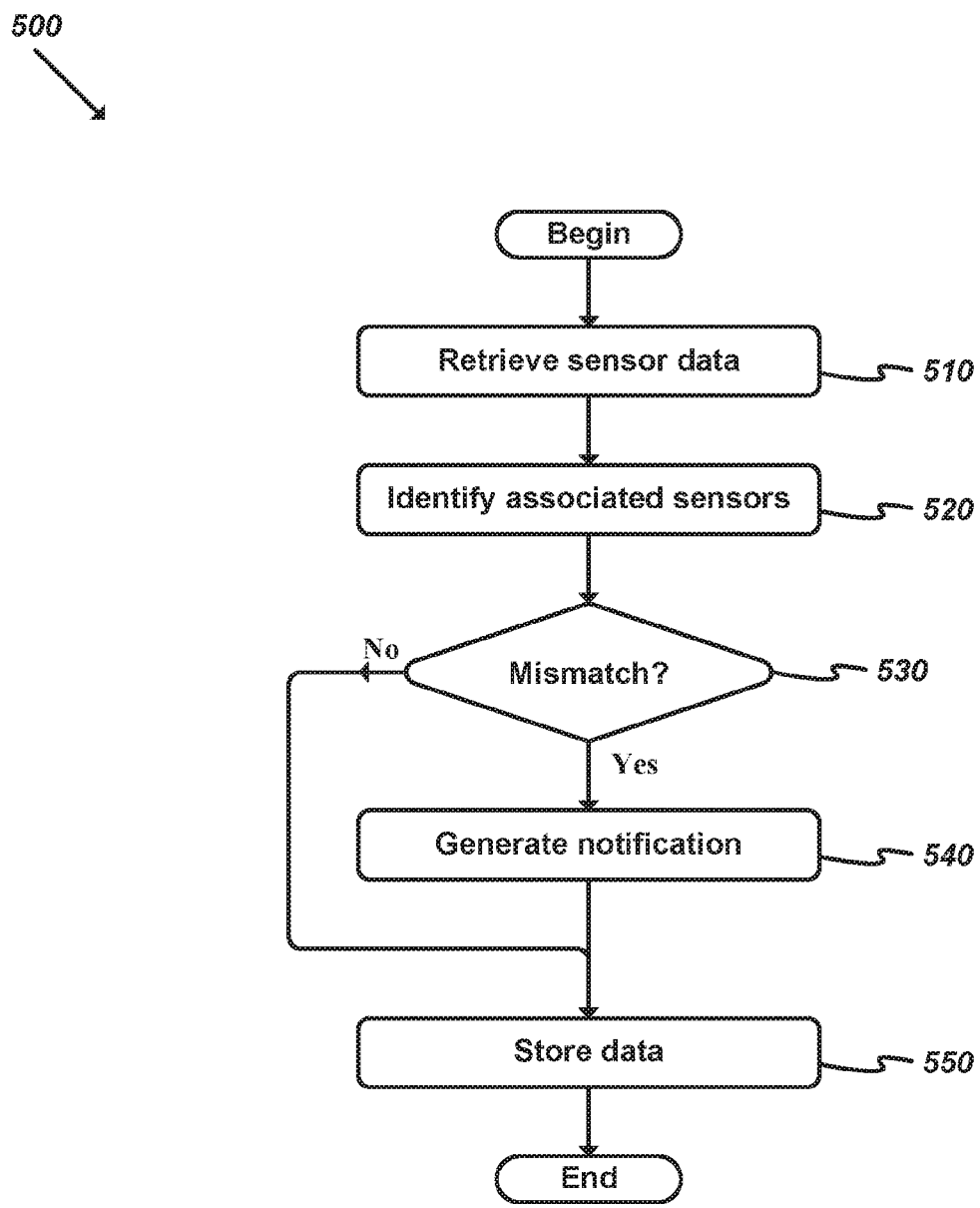
FIG. 5 illustrates a flow chart of an exemplary server-side process that monitors air quality detection equipment.

FIG. 5 illustrates a flow chart of an exemplary server-side process 500 that monitors air quality detection equipment. Such a process may be executed by a device such as server 320 described above and/or other appropriate elements. The process may begin, for instance, when a system of some embodiments is powered on.

As shown, process 500 may retrieve (at 510) sensor data (and/or other data) from one or more devices, such as device 200. The devices may provide data, such as measurements, messages, etc. that may be utilized by the server during operation. Such data may include previously stored information, such as measurements over time, previous messages, etc.

Next, the process may identify (at 520) associated sensors and/or sensor data. Sensors may be associated in various different ways. For instance, a pair of sensors may be associated with a single SRAID device of some embodiments. As another example, multiple devices (and sensors) may be associated with an air flow system (e.g., an HVAC system). As still another example, sensors may be grouped by geographic region, sensor type, measurement range, and/or other relevant factors.

Next, the process may determine (at 530) whether there is a mismatch or other issue with the retrieved associated data. Such a determination may be made based on various relevant criteria. For instance, some embodiments may compare a difference among the associated sensors to one or more threshold values. Such differences may be calculated in various appropriate ways such as subtraction, comparison to an average (e.g., a mean, median, weighted average, etc.) or other statistical measure (e.g., standard deviation, variance, etc.), If the process determines there is a mismatch, the process may generate (at 540) and send one or more notifications, commands, and/or perform other appropriate actions to correct the mismatch. Such actions may include, for instance, directing a fan or other airflow control element to increase or decrease speed, directing a heating element or other appropriate environmental control element to increase a temperature, etc. In some cases, the actions may be directed by an element such as server 320 and carried out by one or more devices such as SRAID device 200. For instance, the server may send a command to an SRAID device which may, in turn, send a command to a local fan or other appropriate element. Alternatively, the server may communicate directly (i.e., without use of an intervening SRAID device) with the fan or other local element. As another example, a message or notification may be sent to a user device, such as "change filter", "replace unit", etc. Such notifications may be associated with mismatches beyond a correctable level, mismatches that persist after automated attempts at correction, and/or other appropriate conditions.

Finally, the process may store (at 550) data associated with the performed operations and then may end. Such data may include, for instance, measurement data, correction data (including actions and results), device data (e.g., type of sensor, sensor ID, location, application setting, etc.), and/or other appropriate data. Such data may be manipulated at the server and used to generate updates that may be sent to the SRAID devices.

In some embodiments, updates may be sent to one or more sensors under various appropriate conditions. For instance, the server may send update information when an SRAID device executes process 400. As another example, the server may send updates after execution of process 500. Such updates may include updates to threshold values, operating parameters, etc.

In some embodiments, the server and SRAID devices may form a two-way communication channel such that the server may receive data and send commands or other instructions to each device as the system is operated.

Processes 400 and 500 may be performed in various different ways without departing from the scope of the disclosure. For instance, the processes, and/or portions thereof, may be performed iteratively and/or based on some criteria. As another example, the operations may be performed in a different order, additional operations may be included, and/or various listed operations may be omitted.

III. Computer System

Many of the processes and modules described above may be implemented as software processes that are specified as one or more sets of instructions recorded on a non-transitory storage medium. When these instructions are executed by one or more computational element(s) (e.g., microprocessors, microcontrollers, digital signal processors (DSPs), application-specific integrated circuits (ASICs), field programmable gate arrays (FPGAs), etc.) the instructions cause the computational element(s) to perform actions specified in the instructions.

In some embodiments, various processes and modules described above may be implemented completely using electronic circuitry that may include various sets of devices or elements (e.g., sensors, logic gates, analog to digital converters, digital to analog converters, comparators, etc.). Such circuitry may be able to perform functions and/or features that may be associated with various software elements described throughout.

Figure 6:
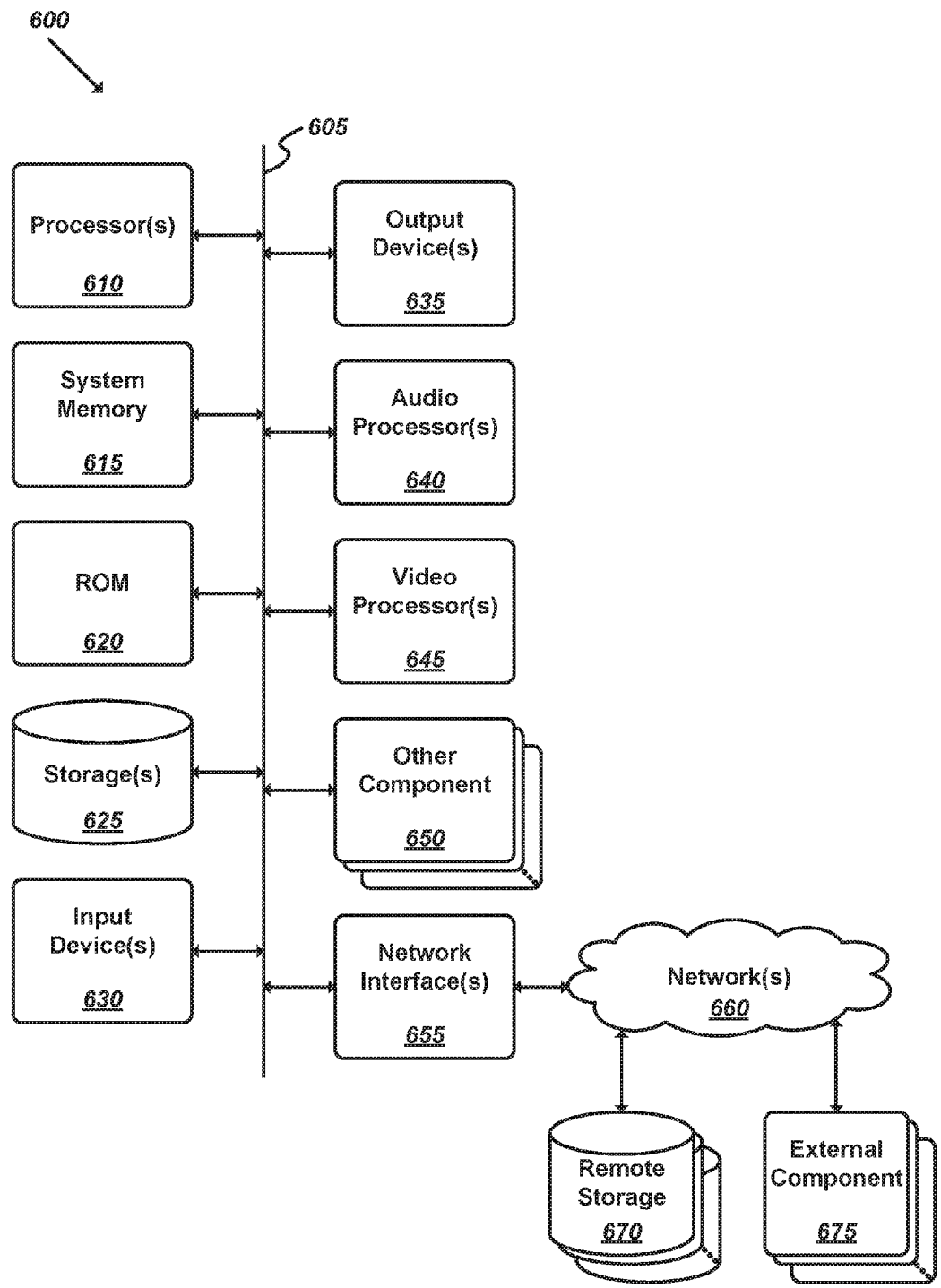
FIG. 6 illustrates a schematic block diagram of an exemplary computer system used to implement some embodiments.

FIG. 6 illustrates a schematic block diagram of an exemplary computer system 600 used to implement some embodiments. For example, the systems and/or devices described above in reference to FIGS. 1A-3 may be at least partially implemented using computer system 600. As another example, the processes described in reference to FIGS. 4-5 may be at least partially implemented using sets of instructions that are executed using computer system 600.

Computer system 600 may be implemented using various appropriate devices. For instance, the computer system may be implemented using one or more personal computers (PCs), servers, mobile devices (e.g., a smartphone), tablet devices, and/or any other appropriate devices. The various devices may work alone (e.g., the computer system may be implemented as a single PC) or in conjunction (e.g., some components of the computer system may be provided by a mobile device while other components are provided by a tablet device).

As shown, computer system 600 may include at least one communication bus 605, one or more processors 610, a system memory 615, a read-only memory (ROM) 620, permanent storage devices 625, input devices 630, output devices 635, audio processors 640, video processors 645, various other components 650, and one or more network interfaces 655.

Bus 605 represents all communication pathways among the elements of computer system 600. Such pathways may include wired, wireless, optical, and/or other appropriate communication pathways. For example, input devices 630 and/or output devices 635 may be coupled to the system 600 using a wireless connection protocol or system.

The processor 610 may, in order to execute the processes of some embodiments, retrieve instructions to execute and/or data to process from components such as system memory 615, ROM 620, and permanent storage device 625. Such instructions and data may be passed over bus 605.

System memory 615 may be a volatile read-and-write memory, such as a random access memory (RAM). The system memory may store some of the instructions and data that the processor uses at runtime. The sets of instructions and/or data used to implement some embodiments may be stored in the system memory 615, the permanent storage device 625, and/or the read-only memory 620. ROM 620 may store static data and instructions that may be used by processor 610 and/or other elements of the computer system.

Permanent storage device 625 may be a read-and-write memory device. The permanent storage device may be a non-volatile memory unit that stores instructions and data even when computer system 600 is off or unpowered. Computer system 600 may use a removable storage device and/or a remote storage device as the permanent storage device.

Input devices 630 may enable a user to communicate information to the computer system and/or manipulate various operations of the system. The input devices may include keyboards, cursor control devices, audio input devices and/or video input devices. Output devices 635 may include printers, displays, audio devices, etc. Some or all of the input and/or output devices may be wirelessly or optically connected to the computer system 600.

Audio processor 640 may process and/or generate audio data and/or instructions. The audio processor may be able to receive audio data from an input device 630 such as a microphone. The audio processor 640 may be able to provide audio data to output devices 640 such as a set of speakers. The audio data may include digital information and/or analog signals. The audio processor 640 may be able to analyze and/or otherwise evaluate audio data (e.g., by determining qualities such as signal to noise ratio, dynamic range, etc.). In addition, the audio processor may perform various audio processing functions (e.g., equalization, compression, etc.).

The video processor 645 (or graphics processing unit) may process and/or generate video data and/or instructions. The video processor may be able to receive video data from an input device 630 such as a camera. The video processor 645 may be able to provide video data to an output device 640 such as a display. The video data may include digital information and/or analog signals. The video processor 645 may be able to analyze and/or otherwise evaluate video data (e.g., by determining qualities such as resolution, frame rate, etc.). In addition, the video processor may perform various video processing functions (e.g., contrast adjustment or normalization, color adjustment, etc.). Furthermore, the video processor may be able to render graphic elements and/or video.

Other components 650 may perform various other functions including providing storage, interfacing with external systems or components, etc.

Finally, as shown in FIG. 6, computer system 600 may include one or more network interfaces 655 that are able to connect to one or more networks 660. For example, computer system 600 may be coupled to a web server on the Internet such that a web browser executing on computer system 600 may interact with the web server as a user interacts with an interface that operates in the web browser. Computer system 600 may be able to access one or more remote storages 670 and one or more external components 675 through the network interface 655 and network 660. The network interface(s) 655 may include one or more application programming interfaces (APIs) that may allow the computer system 600 to access remote systems and/or storages and also may allow remote systems and/or storages to access computer system 600 (or elements thereof).

As used in this specification and any claims of this application, the terms "computer", "server", "processor", and "memory" all refer to electronic devices. These terms exclude people or groups of people. As used in this specification and any claims of this application, the term "non-transitory storage medium" is entirely restricted to tangible, physical objects that store information in a form that is readable by electronic devices. These terms exclude any wireless or other ephemeral signals.

It should be recognized by one of ordinary skill in the art that any or all of the components of computer system 600 may be used in conjunction with some embodiments. Moreover, one of ordinary skill in the art will appreciate that many other system configurations may also be used in conjunction with some embodiments or components of some embodiments.

In addition, while the examples shown may illustrate many individual modules as separate elements, one of ordinary skill in the art would recognize that these modules may be combined into a single functional block or element. One of ordinary skill in the art would also recognize that a single module may be divided into multiple modules.

The foregoing relates to illustrative details of exemplary embodiments and modifications may be made without departing from the scope of the disclosure as defined by the following claims.

We claim:

1. An automated method of detecting measurement inaccuracy in an air quality detection system, the method comprising:
   receiving a first air quality measurement from a first sensor located at a first location along an air flow pathway;
   receiving a second air quality measurement from a second sensor located at the first location along an air flow pathway;
   determining a difference between the first air quality measurement and the second air quality measurement in order to identify a mismatch between the first sensor and the second sensor;
   comparing the mismatch to a maximum threshold value; and
   adjusting at least one physical operating parameter of the air quality detection system if the difference exceeds the maximum threshold value, wherein the at least one physical operating parameter comprises at least one of fan speed and heat.

2. The automated method of claim 1, wherein adjusting the at least one physical operating parameter comprises sending a command to an air flow controller device.

3. The automated method of claim 1, wherein the receiving, determining, comparing, and adjusting are performed by a single smart residue avoidance and inaccuracy detection device.

4. The automated method of claim 1, wherein the receiving, determining, comparing, and adjusting are performed by a plurality of smart residue avoidance and inaccuracy detection devices and at least one server.

5. A system that detects measurement inaccuracy in an air quality detection, the system comprising:
   a plurality of smart residue avoidance and inaccuracy detection (SRAID) devices; and
   a server,
   wherein each SRAID device in the plurality of SRAID devices comprises:
      a first air quality sensor located at a first location along an air flow pathway;
      a second air quality sensor located at the first location along an air flow pathway; and
      a communication module that communicates with the server, and
   wherein each SRAID device in the plurality of SRAID devices:
      retrieves a first measurement from the first air quality sensor;
      retrieves a second measurement from the second air quality sensor;
      generates a first difference between the first measurement and the second measurement;
      determines whether the first difference is greater than a first threshold value; and
      adjusts at least one air flow controller device if the difference is greater than the first threshold value.

6. The system of claim 5, wherein the server:
   compares measurements received from a set of SRAID devices from among the plurality of SRAID devices;
   generates a notification if a difference among the compared measurements is greater than a second threshold value; and
   sends the notification to at least one of a particular SRAID device from among the plurality of SRAID devices and a particular air flow controller device from the at least one air flow controller device.

7. The system of claim 6, wherein the set of SRAID devices is associated with a particular air flow pathway.

8. The system of claim 6, wherein the notification comprises a speed increase command related to the particular air flow controller device.

9. The system of claim 6, wherein the speed increase command is passed from the particular SRAID device to the particular air flow controller device.

10. A smart residue avoidance and inaccuracy detection (SRAID) device comprising:
    a first air quality detection sensor located at a first location along an air flow pathway;
    a second air quality detection sensor located at the first location along an air flow pathway;
    a first mini turbulent generator associated with the first air quality detection sensor;
    a second mini turbulent generator associated with the second air quality detection sensor;
    a controller that:
       receives measurements from the first and second air quality detection sensors;
       calculates a difference between the received measurements;
       adjusts at least one of the first mini turbulent generator and the second mini turbulent generator if the difference exceeds a threshold value; and
       generates a notification if the difference exceeds the threshold value; and
    a communication module that communicates with at least one of a server and an air flow controller device.

11. The SRAID device of claim 10, wherein the notification comprises a speed increase command that is sent by the communication module to the air flow controller device.

12. The SRAID device of claim 11, wherein the speed increase command is sent via the server.

13. The SRAID device of claim 10, wherein the first and second air quality detection sensors are arranged in a serial configuration along an air flow pathway.

14. The SRAID device of claim 10, wherein the first and second air quality detection sensors are arranged in a parallel configuration along an air flow pathway.

* * * * *